United States Patent
Schneeberger et al.

(10) Patent No.: US 11,986,558 B2
(45) Date of Patent: *May 21, 2024

(54) DRUG DELIVERY SYSTEM

(71) Applicants: Laxxon Medical AG, Stetten (CH); Exentis Knowledge GmbH, Stetten (CH)

(72) Inventors: Achim Schneeberger, Vienna (AT); Klaus Kühne, Berlin (DE); Helmut Kerschbaumer, Zürich (CH); Srdan Vasic, Horgen (CH)

(73) Assignees: Laxxon Medical AG, Stetten (CH); Exentis Knowledge GmbH, Stetten (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/863,884

(22) Filed: Jul. 13, 2022

(65) Prior Publication Data

US 2022/0339109 A1    Oct. 27, 2022

Related U.S. Application Data

(62) Division of application No. 16/958,777, filed as application No. PCT/EP2017/084825 on Dec. 29, 2017, now Pat. No. 11,419,824.

(51) Int. Cl.
*A61K 9/20* (2006.01)
*A61K 31/422* (2006.01)
(Continued)

(52) U.S. Cl.
CPC .......... *A61K 9/2077* (2013.01); *A61K 9/2027* (2013.01); *A61K 9/2054* (2013.01);
(Continued)

(58) Field of Classification Search
CPC .. A61K 9/2077; A61K 9/2054; A61K 31/506; A61K 31/519; A61K 31/4985;
(Continued)

(56) References Cited

U.S. PATENT DOCUMENTS 3,854,480 A    12/1974   Zaffaroni
5,656,294 A    8/1997    Friend et al.
(Continued)

FOREIGN PATENT DOCUMENTS

AU    777621 B2    10/2004
CN    1377258 A    10/2002
(Continued)

OTHER PUBLICATIONS

Original and English Translation of Japanese Office Action issued for corresponding Japanese Application No. 2020-555294, dated Jul. 26, 2022.
(Continued)

*Primary Examiner* — Jianfeng Song
(74) *Attorney, Agent, or Firm* — Renner, Otto, Boisselle & Sklar, LLP

(57) ABSTRACT

The present invention relates to a drug delivery system, in particular for a controlled administration of one or more active pharmaceutical ingredients to a body, and further in particular for oral administration of one or more active pharmaceutical ingredients to a body. The system thereby comprises a base component soluble in body fluids and a separate first component soluble in body fluids. The first component thereby comprises a therapeutically effective amount of a first active pharmaceutical ingredient.

18 Claims, 7 Drawing Sheets

Figure 1:
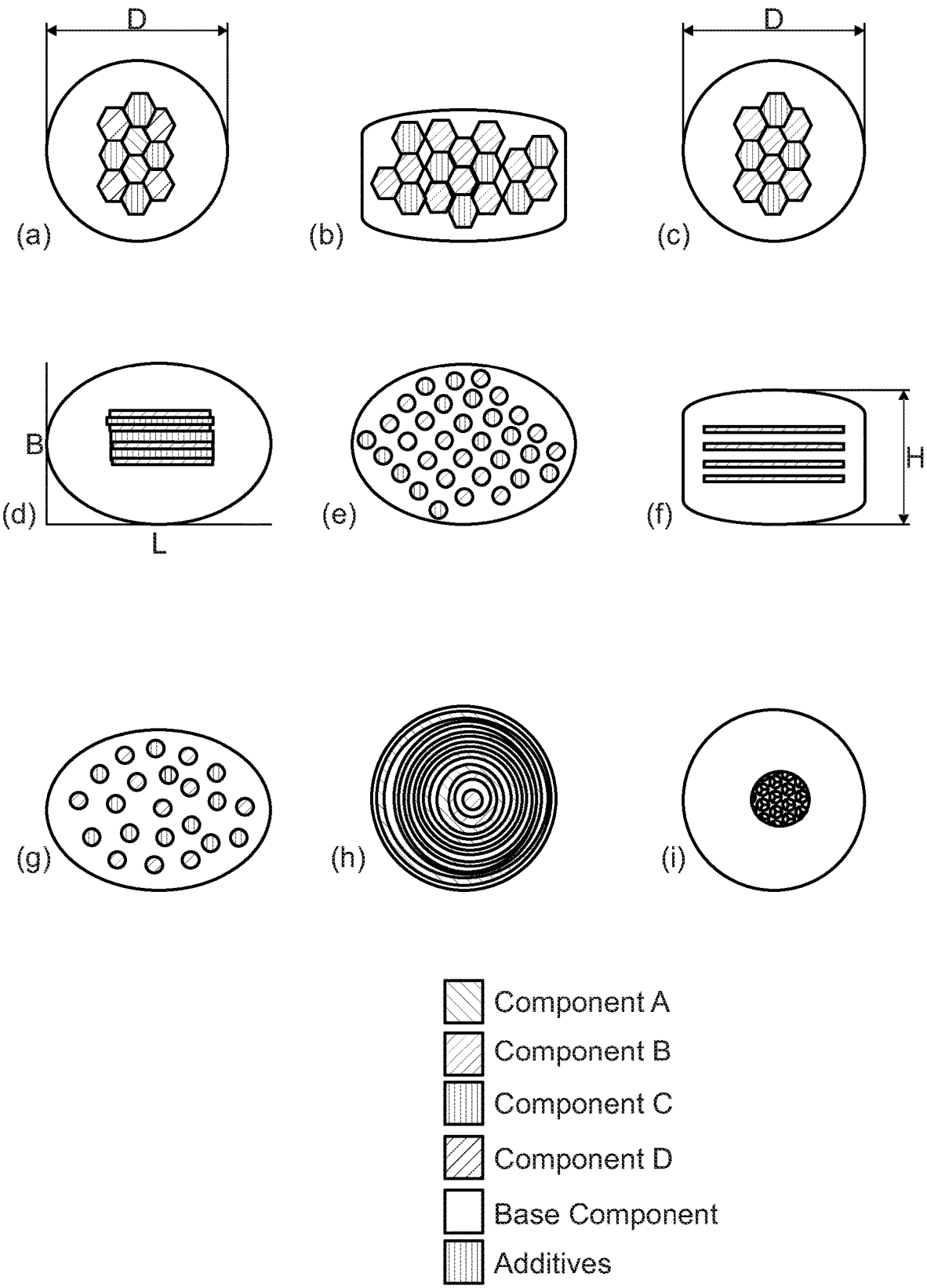

(51) Int. Cl.
*A61K 31/44* (2006.01)
*A61K 31/4439* (2006.01)
*A61K 31/4468* (2006.01)
*A61K 31/496* (2006.01)
*A61K 31/4985* (2006.01)
*A61K 31/506* (2006.01)
*A61K 31/519* (2006.01)
*A61K 31/5377* (2006.01)
*A61K 31/7072* (2006.01)

(52) U.S. Cl.
CPC .......... *A61K 9/2059* (2013.01); *A61K 31/422* (2013.01); *A61K 31/44* (2013.01); *A61K 31/4439* (2013.01); *A61K 31/4468* (2013.01); *A61K 31/496* (2013.01); *A61K 31/4985* (2013.01); *A61K 31/506* (2013.01); *A61K 31/519* (2013.01); *A61K 31/5377* (2013.01); *A61K 31/7072* (2013.01)

(58) Field of Classification Search
CPC .. A61K 9/2027; A61K 9/2095; A61K 9/2059; A61K 31/5377; A61K 31/496; A61K 9/7092; A61K 31/7072; A61K 31/4468; A61K 31/422; A61K 31/4439; A61K 31/44

See application file for complete search history.

(56) References Cited

U.S. PATENT DOCUMENTS

| | | | |
|---|---|---|---|
| 5,674,530 | A | 10/1997 | Amidon et al. |
| 2003/0099708 | A1 | 5/2003 | Rowe et al. |
| 2003/0143268 | A1 | 7/2003 | Lewis et al. |
| 2007/0196491 | A1 | 8/2007 | Venkatesh |
| 2008/0241216 | A1* | 10/2008 | Von Falkenhausen .. A61K 9/70 424/436 |
| 2010/0068271 | A1 | 3/2010 | Kaplan et al. |
| 2010/0093677 | A1* | 4/2010 | Goodhew ............ A61K 31/137 514/212.07 |
| 2011/0237563 | A1 | 9/2011 | Costantini |
| 2015/0056277 | A1 | 2/2015 | Bloemers et al. |

FOREIGN PATENT DOCUMENTS

| | | | |
|---|---|---|---|
| CN | 1761453 | A | 4/2006 |
| CN | 101410093 | A | 4/2009 |
| CN | 103025321 | A | 4/2013 |
| CN | 103648487 | A | 3/2014 |
| DE | 69633721 | T2 | 12/2005 |
| EP | 0169364 | A1 * | 1/1986 |
| EP | 0169364 | A1 | 1/1986 |
| EP | 1216035 | A2 | 6/2002 |
| JP | 2005509001 | A | 4/2005 |
| JP | 2006-517514 | A | 7/2006 |
| JP | 2013-521821 | A | 6/2013 |
| JP | 2014-533656 | A | 12/2014 |
| WO | 1993007861 | A1 | 4/1993 |
| WO | 1999008662 | A1 | 2/1999 |
| WO | 2001022947 | A2 | 4/2001 |
| WO | 2003037607 | A1 | 5/2003 |
| WO | 2003041690 | A2 | 5/2003 |
| WO | WO2003037607 | * | 5/2003 |
| WO | 2004/028512 | A1 | 4/2004 |
| WO | 2004/112746 | A1 | 12/2004 |
| WO | 2007011473 | A1 | 1/2007 |
| WO | 2011/117634 | A2 | 9/2011 |
| WO | 2013/081177 | A1 | 6/2013 |

OTHER PUBLICATIONS

Original and English Translation of The First Chinese Office Action issued for corresponding Chinese Application No. 201780098315.6, dated Mar. 2, 2022.

Japanese First Office Action and English Translation issued for corresponding JP Application No. 2020-555294 dated Jan. 4, 2022.

International Search Report and Written Opinion for corresponding International Patent Application No. PCT/EP2017/084825 dated May 2, 2018.

International Preliminary Report on Patentability for corresponding International Patent Application No. PCT/EP2017/084828 dated Mar. 31, 2020.

* cited by examiner (1)

(2)

(3)

—marking
 —marking
 —marking
 —marking

DRUG DELIVERY SYSTEM

1. RELATED APPLICATION DATA

This application is a division of U.S. patent application Ser. No. 16/958,777, filed Jun. 29, 2020, which is a national phase of International Application No. PCT/EP2017/084825, filed Dec. 29, 2017, and published in English under International Publication No. WO 2019/129360 A1 on Jul. 4, 2019, all of which are incorporated herein by reference.

2. FIELD OF THE INVENTION

The present invention relates to a drug delivery system for a controlled, preferably systemic administration of one or more active pharmaceutical ingredients to a body, in particular (but not limited to) for oral administration.

3. TECHNICAL BACKGROUND

A drug or a pharmaceutical drug, is commonly used for diagnosing, curing, treating or preventing diseases. An active pharmaceutical ingredient (API) may be the part of any drug that produces its effects. Some drugs may have multiple APIs to treat different symptoms or act in different ways. Thus, one or more APIs may be delivered by a drug. The delivery of drugs, or drug delivery, may refer to the transportation of a pharmaceutical compound into the body of a patient as needed to safely achieve its desired (therapeutic) effect. The delivery or administration of a drug into the body of a patient may be performed in various ways. The routes of administration include, among others, the intravenous (into the blood compartment through the puncture of a vein) and oral route (through the mouth of the patient, e.g. to enter via the oral mucosa or pass on into the gastrointestinal tract to reach the blood compartment via the gastric or intestinal mucosa). Drugs can further be administered by inhalation, by injection into tissues (e.g., subcutaneous, intramuscular) or by topical application (e.g., creams for use on the skin). Drugs can be provided in different dosage forms. The dosage forms may comprise, among others, pills, tablets, capsules, solutions, dispersions, emulsions, implants.

A tablet may be a pharmaceutical dosage form. A tablet may be a solid unit dosage form of a pharmaceutical drug comprising an API, with or without suitable excipients. Tablets may be prepared either by molding or by compression. Upon manufacturing of a tablet, the main guideline is commonly to ensure that the appropriate amount of active pharmaceutical ingredient(s) is in each tablet. Therefore, all ingredients should be well mixed. Thereby, a homogeneous mixture of the ingredients is obtained. A particular amount of the mixture may then be compressed in order to obtain a tablet. Thus, the API is typically homogeneously distributed throughout the tablet, or parts of it.

Upon application of a tablet, for example upon oral administration, the tablet may dissolve and thereby the API may be released. It then passes the intestinal mucous membrane to reach the blood compartment and finally the tissue of action. With the common drug delivery systems, the concentration of the API within the blood compartment is typically such that, for a particular period of time only, it is above the efficacy threshold of the given API. During this period, the release of the API out of the drug delivery system into the gastrointestinal tract is however typically much higher than actually required, whereby the excess amount of the API may (i) not pass the membrane in sufficient amounts and be picked up by the body and, thus, may be excreted of (ii) may reach the blood compartment/the tissue to result in toxic effects.

According to the respective background of the drug application, or the particular therapeutic program, it may be desirable to have a particular release profile of the API. It may, for example, be desirable to release the API at the constant rate over a prolonged period of time. In other scenarios, it may be desirable to provide for a particularly slow release of an API to a body, with a release rate slightly above the efficacy threshold of the API, wherein the rate of release may be approximately independent of time. In further scenarios, it may be desirable to release the API at particular intervals, for example intermittently over time. In further scenarios, it may be desirable to release several APIs one after the other, or simultaneously at individual release rates, with API-specific release profiles.

Release of APIs out of common tablets, which are characterized by a homogeneous distribution of the APIs due to the requirements and limits of the conventional manufacturing technologies, is mainly driven by the size of the disintegrating tablet, in particular, the surface that is exposed to the surrounding fluid. As such it is predefined by the form and size of the tablet and fixed, with for example a high release at the beginning and lowering over time. The resulting blood/tissue concentrations of the API may thereby well exceed the respective efficacy threshold, in order to obtain a desired period of concentration above said threshold.

Such a release profile is particularly disadvantageous for APIs with a narrow therapeutic window (that is little difference between therapeutic and toxic dose). APIs with a narrow therapeutic index (NTI) include aminoglycosides, ciclosporin, carbamazepine, digoxin, digitoxin, flecainide, lithium, phenytoin, phenobarbital, rifampicin, theophylline, warfarin.

Reference U.S. Pat. No. 3,854,480 describes a drug delivery system for releasing an active pharmaceutical ingredient at a controlled rate for a prolonged period of time. The drug delivery system thereby comprises a solid inner matrix material having solid particles of the drug distributed therethrough, and an outer polymeric membrane, which is permeable and insoluble in body fluids and which surrounds the inner matrix. The outer polymeric membrane thereby continuously meters the flow of drug from the inner matrix material to the exterior of the system at a controlled and constant rate over a prolonged period of time. However, the drug delivery system according to U.S. Pat. No. 3,854,480 does not allow for more elaborate release profiles. Further, the administration of an insoluble polymeric membrane to the body of a patient may be disadvantageous.

Reference U.S. Pat. No. 5,674,530 A relates to a drug delivery system, wherein a first water permeable capsule half is filled with a drug and an osmotic agent. Reference US 2010/0068271 A1 relates to osmotic delivery systems employed in tablets, being divisible into two useable half-strength tablets. The release by means of osmotic effects is dependent, among others, on the environment of the drug delivery system in the patient, making a precise drug release at a desired target challenging. Thus, it is difficult to achieve a controlled and precise drug release with such systems. Furthermore, such systems do not allow for more elaborate release profiles.

Reference WO 1993/007861 A1 relates to drug delivery systems involving microcapsules or microspheres. Thereby multi-phase microspheres are described to include a molecular compound contained within a fixed oil within a polymeric matrix. The molecular compound may first have to traverse a water-oil barrier, and the polymer barrier of the polymer matrix, before it can diffuse out of the microsphere. Thereby, a constant and fixed rate of delivery of a molecular compound can provided without sacrificing high drug loading efficiency in the microsphere. However, this prior art system does not allow for more elaborate release profiles.

Reference WO 1999/008662 A1 relates to a drug delivery system suitable for oral administration that facilitates a two-step release of an active agent. A drug delivery system disclosed therein comprises a first drug compartment, a first polymer compartment substantially enveloping the first drug compartment, a second drug compartment enveloping the first polymer compartment, and a second polymer compartment enveloping the second drug compartment. The second polymer compartment, which may be of one or more water insoluble polymers, controls the release of an active agent from the second drug compartment. However, this prior art system does not allow for more elaborate release profiles.

The present invention aims at overcoming the disadvantages outlined above. Thus, one problem underlying the present invention is to provide a more efficient drug delivery system which can advantageously provide for a controlled administration of one or more active pharmaceutical ingredients to a body, with an application-tailored, therapy-tailored and/or API-specific release profile. A further object of the present invention is to provide a drug delivery system which allows for a controlled administration of several APIs to a body, such that the APIs are released relative to each other in a defined manner, preferably with desired API-specific release profiles. A general object of the invention can be formulated as to optimize pharmacokinetics and pharmacodynamics.

These and other objects, which are apparent for the person skilled in the art from the following description, are solved by a drug delivery system according to claim 1, and the usage thereof according to claim 31.

4. SUMMARY OF THE INVENTION

The present invention relates to a drug delivery system. The drug delivery system may be a drug and may allow for transporting an active pharmaceutical ingredient (API) in the body of a patient as needed to safely achieve its desired therapeutic effect. The drug delivery system may thereby include an API, or several APIs, or other ingredients such as vitamins and minerals. The drug delivery system may be a bioerodible drug delivery system. Thus, the drug delivery system may erode upon application thereof to a body of a patient, and may, for example, dissolve upon application, e.g. in the mouth of the patient. The drug delivery system according to the present invention is particularly suited for a controlled administration of one or more APIs to a body. The body may be the body of a patient, which may be a human or an animal. Further in particular, the drug delivery system may be used for oral administration of one or more APIs to a body, whereby the system may dissolve in the mouth of the patient. Thus, with the drug delivery system according to the present invention, an API can be administered in a controlled manner, depending on the particular therapy or application case.

The drug delivery system according to the present invention comprises a base component, which is soluble in body fluids. As an example, body fluids may include blood, or body tissue fluids. Body fluids encountered will vary according to the route of administration. Upon oral intake, the composition of the outer layer may determine whether dissolution of the drug delivery system will start in the mouth (dissolution in saliva) or later along the journey of the system through the gastrointestinal tract, in particular, the stomach (acidic milieu), the ileum, the jejunum or other places. Likewise, the drug delivery system may be directly placed into tissues (e.g., subcutaneously, intramuscularly) or body cavities (e.g., pleural space) or into the cerebrospinal fluid spaces. Upon placement into the ventricles, the drug delivery system may dissolve within the cerebrospinal fluid and any released API may reach the brain tissue. Placement into natural body cavities (e.g., pleural space, peritoneal space) is meant to reach these localizations at high quantities. Another possibility may comprise dissolution within the airways upon inhalation. The person skilled in the art will appreciate that the dissolution characteristics of the drug delivery system may be chosen such that a suitable release of the API is obtained, depending on the respective therapy or application. Thereby, a rather instant or a rather slow dissolution can be chosen.

Furthermore, the drug delivery system of the present invention comprises a separate first component soluble in body fluids. Thus, the first component may dissolve in a manner similar to the base component. Preferably, the base component and the first component can dissolve in the same body fluid. The first component is not mixed with the base component in a classical manner to form a homogeneous mixture, but is provided as a component separate to the base component. Thus, within the drug delivery system, the base component can be distinguished from the first component.

Furthermore, according to the present invention, the first component comprises a therapeutically effective amount of a first active pharmaceutical ingredient. Accordingly, the first component may comprise the API which is to be delivered or administered by means of the drug delivery system. The first API may be homogeneously distributed within the first component. The person skilled in the art understands that the first component may comprise several APIs, which may be homogeneously distributed within the first component. Also, the base component may comprise an active pharmaceutical ingredient.

Furthermore, according to the present invention, the first component is inhomogeneously arranged in the base component. Accordingly, the base component and the separate first component are not provided as a homogeneous mixture in the drug delivery system, but are provided separately from another, preferably in a particular manner, wherein the first component is inhomogeneously arranged in the base component. The first component may be provided inhomogeneously or discontinuously along one, two or most preferred three spatial or orthogonal directions in the base component. By arranging the components in this manner, the first component is being arranged in the system in such a controlled and desired manner, so that no homogeneous distribution of the first component (and thus of the first API) is present throughout the system. Instead, the inhomogeneity is specifically constituted by the particular arrangement of the components. Although the base component and the first component are provided as separate components, the first component can be arranged inhomogeneously within a matrix formed of the base component. For example, the amount of the first component arranged within the base component may increase gradually along a particular direction throughout the system.

The base component may thereby be provided or considered as a three-dimensional body, and the separate first component may be inhomogeneously arranged throughout the base component. Thus, the main body of the drug delivery system may be formed of the base component, and one or more particular parts of the drug delivery system, which may be only of marginal size, may be formed of the first component. The base component and the first component may be arranged on a virtual two- or three-dimensional grid, wherein each pixel of the grid may be occupied by the base component or by the first component. Thus, the first component is arranged inhomogeneously in the base component, and thus may be inhomogeneously arranged in the drug delivery system itself. The size or volume of each of such a pixel may be in the range of 1 µm$^3$ to 1 cm$^3$, preferably in the range of 10 µm$^3$ to 100 mm$^3$, preferably in the range of 100 µm$^3$ to 10 mm$^3$, and most preferred of about 1 mm$^3$. Preferably, the first component and the base component are arranged such that two- or three-dimensional structures formed by the components in the drug delivery system may feature a resolution in the range of 10 dpi to 10000 dpi, further preferred 100 dpi to 5000 dpi, further preferred 200 dpi to 2000 dpi, further preferred 500 dpi to 1000 dpi.

Due to the particular arrangement of the base component and the first component, it is possible to obtain a particularly desired release of the first API. As both of the base component and the first component are soluble in body fluids, it can be controlled at what time and at which rate the first API is released from the drug delivery system, namely by controlling the inhomogeneous arrangement of the first component with regard to the base component. This allows for providing a drug delivery system with an optimal API release for a controlled administration of a given API to a body. Preferably, the release of the API is determined only by the dissolution characteristics of the components and the form of the drug delivery system. No further release agents are required, such as e.g. osmotic agents for releasing the API.

As the common principle of a homogeneous distribution of an API throughout a drug delivery system is suspended, it is possible to provide a particular arrangement of the API in the system to obtain a drug delivery system with a customized release profile of the API. The component comprising the API may be arranged such that a steady release of the API is obtained, with a release that preferably results in a blood/tissue concentration slightly above the efficacy threshold of the API. Thereby, as compared to the common drug delivery system with a homogeneous distribution of the API, an effectively less amount of API is advantageously required with the drug delivery system according to the present invention, while the same clinical results are maintained with lower side effects.

According to the present invention, the inhomogeneous distribution of an API in the drug delivery system is utilized in a standardized manner, whereby a particular arrangement of the components is chosen or set. This concept allows for providing drug delivery systems with the advantageous release profiles as described herein. The standardization, definition or specification of the arrangement of the components and thus the standardization, definition or specification of the inhomogeneity of the API allows for producing such drug delivery systems uniformly in high quantity, also in a mass production.

Any or all of the components of the drug delivery system may comprise water, polyvinylpyrrolidone, citric acid, hypromellose, stearate, silic acid, glycerol, Hydroxypropyl cellulose, hydroxypropyl methylcellulose, starch, cellulose-crosscaramelose, glycol, crystalline gelatin, collagen, hydroxyapatite, hydrocarbonate, lactide, lactic acid, silica, polaxamers, xylitol, erythritol, ethanol, isopropanol, triacetin, aspartame, sodium bicarbonate, and/or acetone.

In a preferred embodiment, the concentration of the first API varies throughout the drug delivery system, or further preferred varies throughout the body defined by the base component. For example, the first component may be provided at central parts of the drug delivery system only. Thus, particular regions of the drug delivery system may be identified having a rather high concentration of the first API, and particular regions may be identified having a rather low (or even no) concentration of the first API. Thereby, whilst taking into consideration the particular form or shape of the drug delivery system, as well as the dissolution characteristics of the base component and first component, it can be precisely controlled when and how the API is eventually released.

Further preferred, the concentration of the first API is highest at a center, at an edge or at an intermediate region of the system. Thus, for example, if the drug delivery system is provided in form of a tablet, the first component may be arranged such that a peak concentration of the first API is provided at the center or a central part of the tablet. Accordingly, upon administration of the tablet and dissolution of the base component and the first component, the release of the first API may increase over time, or may remain approximately constant over time, also depending on the shape of the drug delivery system. This allows for obtaining a desired, specific release of the API.

Further preferred, a gradient of the concentration of the first API increases towards or increases away from a center of a drug delivery system. For example, the amount of the first component may increase towards the center of the drug delivery system. For example, if the drug delivery system is provided in form of a spherical tablet, the arrangement of the first component and thus of the first API may be such that the release rate is approximately constant upon application of the drug delivery system, when the concentration increases towards the center of the tablet. By adjusting the concentration profile of the API throughout the drug delivery system, the release profile of the API can be well controlled.

Further preferred, a concentration profile of the first API throughout the system comprises a smooth transition to an area of increased concentration. Thus, the concentration profile may comprise a smooth transition between an area of low (or possibly no) concentration, and an area of high concentration. For example, the amount of the first component may increase gradually towards the center of the drug delivery system. A smooth transition may be defined by the absence of abrupt or discontinuous steps in the concentration profile. The concentration profile may represent the profile of the concentration of the first API diagonally across the drug delivery system, for example from one edge of the system to its center, or possibly extending through the entire drug delivery system. With such smooth transitions, it is possible to obtain a smooth onset of the release of the API upon dissolution of the respective components.

Further preferred, a concentration profile of the first API throughout the system comprises more than one area of increased concentration. Thereby, several dosages of the API can be administered over time with the drug delivery system. Particularly preferred, the deposition of the first API within the drug delivery system along the dissolution direction (e.g. from the periphery to the center) may be discontinuous and repetitive in an onion skin type manner. In each such shell of the system, the first component may be provided inhomogeneously, such that a release of the first API is preferably not starting in an abrupt manner, but can be set such that the release starts and/or ends gradually. Thereby, the release of the API may occur in distinct waves, intervals with high release of the first API are followed by intervals with low or no release. Further, the API can be administered in several phases over time. These phases (and in particular their onset) can be controlled by controlling the arrangement of the areas of increased concentration within the system.

Further preferred, the variation of the concentration of the first API throughout the system is at least 5%, further preferred at least 10%, further preferred at least 15%, further preferred at least 20%, further preferred at least 25%, further preferred at least 30%, further preferred at least 35%, further preferred at least 40%, further preferred at least 45%, further preferred at least 50%, further preferred at least 55%, further preferred at least 60%, further preferred at least 65%, further preferred at least 70%, further preferred at least 75%, further preferred at least 80%, further preferred at least 85%, further preferred at least 90%, further preferred at least 95%, further preferred approximately 100%. Further preferred, the variation of the concentration of the first API throughout the system is at most approximately 100%, further preferred at most 95%, further preferred at most 90%, further preferred at most 85%, further preferred at most 80%, further preferred at most 75%, further preferred at most 70%, further preferred at most 65%, further preferred at most 60%, further preferred at most 55%, further preferred at most 50%, further preferred at most 45%, further preferred at most 40%, further preferred at most 35%, further preferred at most 30%, further preferred at most 25%, further preferred at most 20%, further preferred at most 15%, further preferred at most 10%, further preferred at most 5%. Thus, the variation of the concentration can be set in a controlled manner, by providing a respective local arrangement of the first component relative to the base component, to eventually obtain a desired controlled administration of the first API. The variation of the concentration of the first API may be defined as the difference of the maximum concentration and the minimum concentration of the API in the system. In this context, the concentration may be the mass-specific concentration. The respective sampling volume for measuring the concentration may be any suitable volume, and may for example be of 1 $\mu m^3$. For example, if the highest concentration in a sampling volume in the system is of about 80%, and the lowest concentration in a sampling volume in the system is of about 10%, then the variation may be 70%. Thus, for example, throughout the drug delivery system, the concentration of the first API may be at least 10%, and at a central part of the drug delivery system, the concentration of the first API may increase to 80%.

Further preferred, the concentration profile of the first API is such that upon application of the system, the first API is released from the system at a predetermined release profile, which further preferred comprises a section with a release at a constant rate. Accordingly, the first component may be arranged such within the base component that upon application of the drug delivery system, and upon dissolution of the base component and first component, a particular release profile of the API is obtained, with a constant release section in a preferred embodiment.

Particularly preferred, the first component is arranged in the base component such that upon dissolution of the system or the components, the total amount of the first API at an outer surface of the system remains approximately constant for a predetermined time, wherein the predetermined time is preferably in the range of 1 second up to 180 days. For example, the amount of the first component may increase towards central parts of the drug delivery system. The person skilled in the art understands that depending on the respective application and the form of the drug delivery system, rather longer or rather shorter release periods may be applicable. For example, if the drug delivery system is provided in form of an implant, the API may be release during an extended period of up to 180 days. If the drug delivery system is provided in form of a tablet, for example, the API may be released during a period of up to 12 hours. Accordingly, further preferred, the predetermined time of approximately constant release is in the range of 5 seconds to 24 hours, further preferred 10 seconds to 12 hours, further preferred, 1 minute to 6 hours, further preferred 10 minutes to 1 hour. Accordingly, in the exemplary case of a spherical tablet, a gradient of the concentration of the first API may point inwards, so that the amount of API at the surface of the system remains constant when the system is dissolving, i.e. when the volume and surface of the system shrinks. Hence, the first component may be arranged such that eventually the concentration of the first API depends on the distance to the surface of the system. Accordingly, by inhomogeneously arranging the first component in the base component, a constant release of the first API can be set.

Further preferred, the concentration profile of the first API is such that upon application of the system, the first API is released at two or more dosages, wherein release of the first API at one of the dosages starts preferably 1 second to 10 days (the upper value may for example apply if the drug delivery system is provided as an implant), more preferably 2 seconds to 1 day, more preferably 5 seconds to 12 hours, more preferably 10 seconds to 6 hours, more preferably 20 seconds to 2 hours, more preferably 1 minute to 1 hour, and most preferred 10 minutes to 30 minutes before release of the first API at another one of the dosages. For example, the first component may be provided at several, separated locations towards a center of the drug delivery system Thus, for example, if the drug delivery system is provided in form of a tablet, and upon oral administration of the tablet, the first API may be released at a first dosage shortly after administration, before the first API is released at a second dosage at a later time. The dosages may be uniform or may vary among each other. Any duration of release of an API mentioned herein may be measured by means of dissolution tests, for example according to USP-Guideline "General Chapter <711> Dissolution".

In a further preferred embodiment, the base component envelops the system and the first component is not arranged at an outer face of the system. Accordingly, the first component comprising the first API may be provided such that it cannot be accessed from the outside, at least prior to the application of the system. Thus, the first API can be effectively sealed from the environment, reducing the risk of contamination. Furthermore, if for example provided in form of a tablet, the dissolution of the first component is delayed upon oral administration, as the base component has to (at least partially) dissolve first. Thus, a delayed administration of the first API can be obtained. Preferably, the drug delivery system is configured such that release of the first API starts 1 second to 1 day, further preferred, 10 seconds to 12 hours, further preferred 30 seconds to 6 hours, further preferred 1 minute to 4 hours, further preferred 10 minutes to 2 hours, further preferred 30 minutes to 1 hour after application of the drug delivery system.

In a further preferred embodiment, the drug delivery system may further comprise a separate second component soluble in body fluids, wherein the second component comprises a therapeutically effective amount of a second active pharmaceutical ingredient. Thus, the drug delivery system allows for a controlled administration of several APIs in particular applications. The APIs may interact after dissolution of the respective component, and may thereby provide for a synergetic effect in the body. The first and second API may differ in form as well as in concentration.

The person skilled in the art understands that the provisions given herein with regard to the first component and the first API may similarly apply in an analogous manner to the second component and the second API. The person skilled in the art understands that the drug delivery system may comprise further components comprising further active pharmaceutical ingredients, e.g. a third component comprising a third API, a fourth component comprising a fourth API, and so on.

Further preferred, the second component may be inhomogeneously arranged in the base component. Thus, the release of the first API and the second API from the drug delivery system can be controlled also relatively to each other by controlling the inhomogeneous arrangement of the respective first and second components in the base component. The above explanation with regard to the inhomogeneous arrangement also applies here.

Further preferred, a concentration profile of the first API throughout the system is different than a concentration profile of the second API throughout the system. For example, the amount of the first component may increase towards a center of the drug delivery system and the amount of the second component may decrease towards the center of the drug delivery system. Accordingly, the drug delivery system can be designed such that the first API and the second API are released to the body at different dosages.

Further preferred, the first component and the second component may be arranged in a discontinuous manner within the drug delivery system such that the first active is released for a distinct period of time upon the start of the dissolution of the system, which typically occurs from the periphery. Similar to an onion skin type arrangement, the layer with the first component may be adjacent to another layer containing either no API or the second API, for example. By varying parameters like the thickness of the layers, their composition, and the distribution of the APIs within the layers, the release of the APIs may be controlled.

Further preferred, the first component and the second component are arranged in the system such that upon application of the system, release of the first API starts before release of the second API. For example, the second component may be arranged closer to the center of the drug delivery system, while the first component may be arranged further to the edge of the drug delivery system. The release of the first API may further preferred start 1 second to 10 days (the upper value may for example apply if the drug delivery system is provided as an implant), more preferably 2 seconds to 1 day, more preferably 5 seconds to 12 hours, more preferably 10 seconds to 6 hours, more preferably 20 seconds to 2 hours, more preferably 1 minute to 1 hour, and most preferred 10 minutes to 30 minutes before release of the second API. Accordingly, due to the particular inhomogeneous or discontinuous arrangement of the first and second components in the base component, preferably with regard to the dissolution direction, it can be controlled at what time the respective first and second APIs are released relative to one another. Depending on the spatial arrangement of the first and second APIs within the layers, the release of the two APIs may be separated by a defined time interval or the release of the first API may continue when the release of the second API starts. Thereby, particular synergetic effects of the APIs may be obtained. Generally, the APIs may be released to the body within hours, days and months, depending on the individual form of application.

Preferably, the first component and the second component are arranged in the system such that upon application of the system, a release profile of the first API differs from a release profile of a second API. For example, the first API may be released at a rather constant rate, while the second API may be released intermittently. This allows for designing an elaborate drug delivery system.

In a preferred embodiment, the total amount of the first API in the system is between 1 μg and 100 g, preferably between 10 μg and 10 g, more preferably between 100 μg and 1 g, more preferably between 500 μg and 500 mg, more preferably between 1 mg and 100 mg, more preferably between 10 mg and 50 mg. The person skilled in the art understands that any description with regard to the first API may also apply to a possible second or further APIs provided in a second or further components of the drug delivery system.

In a further preferred embodiment, one or more of the components comprises a ceramic, metal, polymer (preferably polymer acrylate) and/or minerals.

In a preferred embodiment, one or more of the components comprises a disintegration agent, which may facilitate dissolution of the respective component. The disintegration agent may comprise cellulose (preferably microcrystalline cellulose), croscarmelose sodium, crospovidone, starches (preferably modified starches), cross-linked polyvinylpyrrolidone, sodium starch glycolate, and/or sodium carboxymethylcellulose.

Preferably, one or more of the components may comprise one or more constituents selected from the following list: colorant, sweetener, flavor, antimicrobial preservative (e.g. sorbic acid, benzoic acid, parabens, scrose, benzalkonium chloride), chemical stabilizers which may be used to increase the chemical stability of the API (e.g. antioxidants such as ascorbic acid or sodium metabisulfite, chelators such as ethylenediaminetetraacetic acid), viscosity modifiers which may be used to reduce the sedimentation of particles (e.g. polymeric materials or inorganic materials such as clay), cellulosic materials which may be used as viscosity enhancers in suspensions (e.g. cellulose, cellulose ethers, alginic acid).

Preferably, one or more of the components may comprise one or more excipients selected from the following list: filler (e.g. lactose, sucrose, glucose, mannitol, sorbitol, calcium carbonate, cellulose), solution binder (e.g. gelatin, polyvinylpyrrolidone, cellulose derivative, polyethylene glycol), dry binder (e.g. cellulose, polyethylene glycol, methylcellulose), glidant (e.g. silica, magnesium stearate, talc).

In a preferred embodiment, the first component is provided in a geometrical shape. The shape may preferably be a tube (which may be a hollow tube), a spot (which may be a local, small cluster or agglomeration), an oval (e.g. in the shape of an open circle or ellipse), a plate, and/or a polygon (e.g. in the shape of a square). Thus, the first component may be provided in such a shape that a desired release of the first API is obtained, possibly even with regard to further APIs provided in further components of the system. Within the particular geometrical shape, the concentration of the API may vary.

In a preferred embodiment, the drug delivery system further comprises a marking component optically different from the base component. The marking component may be arranged such that it forms a two-dimensional pattern on the surface of the system, which may preferably be visible from the outside. The marking component may have a different color than the base component. By providing this marking component with a particular and desired two-dimensional pattern, it is possible to provide the drug delivery system with a predefined symbol, logo, brand name, or the like. This allows for providing a sort of security feature, which allows for a user to authenticate the origin of the drug delivery system.

In another preferred embodiment, the first component is optically different from the base component and is arranged such that it forms a two-dimensional pattern on the surface of the system, which pattern may preferably be visible from the outside. The first component may have a different color than the base component. In this case, the logo or the like may be formed by the first component, to also provide a sort of security feature.

Further preferred, the two-dimensional pattern is a discontinuous pattern, and may thus be due to a inhomogeneous arrangement of the respective component within the base component. This allows for increasing the strength of the authentication level of the security feature, and increases the confidence of the user in the product.

In a preferred embodiment, the drug delivery system is in the form of a tablet, a capsule, a disc, a film, an implant, a subcutaneous implant, a patch, pellets or granules. Thus, the drug delivery system according to the present invention may be provided in various forms, and thereby allow for a desired administration and desired release of an API according to the particular therapeutic application.

Preferably, the drug delivery system features a structured surface. For example, the surface of the drug delivery system may comprise protrusions and recesses formed thereon. Thereby, the surface of the resulting drug delivery system can be enlarged, so that eventually a high release of the respective API can be provided for.

It will be appreciated that the drug delivery system according to the present invention is not limited to a particular API. Generally, any suitable API, which can be provided in a respective component to be inhomogeneously arranged within a base component, can be used. For example, the API may be any of anti-infectives, anti-inflammatories, cardioactive agents, neuroleptic agents, or even nutritional agents. The skilled person understands that this list is not limiting. Further, the drug delivery system according to the present invention may comprise further components or substances, for example additives or the like.

In a preferred embodiment, the first API may be any of anthelmintic agents, narcotics and narcotic antagonists; antihistamines, adrenergic agents, adrenergic blockers sedative hypnotics, CNS agents, analeptics, antiparkinson agents, steroids, coronary vasodilators, anticoagulants, antihypercholesterolemics, antibiotics, antifungal agents, antiviral agents, bone growth promotants, anticancer agents, vitamins, antiinflammatory agents, or antihypertensive agents. In a preferred embodiment, the first API may comprise Pregabalin, Lurasidon, Fentanyl, Rivaroxaban, Sildenafil/Tadalafil, Desatinib, Sorafenib, Varenicline, Memantine, Dexlansoprazole, Sunitinib, Nebivolol, Zolmitriptan, Sitagliptin, Lacosamid, Desvenlafaxin, Lenalidomid, Ledipasvir/Sofosbuvir, Aripiprazole, Levodopa, or Ondansetron/Granisetron. Again, the skilled person understands that this list is not limiting.

In a preferred embodiment, the drug delivery system is produced with a screen-printing technique. Using such a screen-printing technique allows for precisely controlling the arrangement of the first component within the base component of the drug delivery system. A particular mesh can be used for arranging the components in the drug delivery system with the screen-printing technique. The components may thereby be provided in forms of pastes, which are arranged relatively to one another with the screen-printing technique. In this case, the API can be soluble in the respective paste.

Further preferred, the system is produced by alternatingly performing the following steps of screen-printing and curing a base paste comprising the base component, and screen-printing and curing a first paste comprising the first component. The person skilled in the art understands that also further pastes may be used to, for example, provide a second component with a second API.

The present invention further relates to the use of a drug delivery system as described above for a controlled administration of one or more APIs to a body.

5. DESCRIPTION OF PREFERRED EMBODIMENTS

Figure 2:
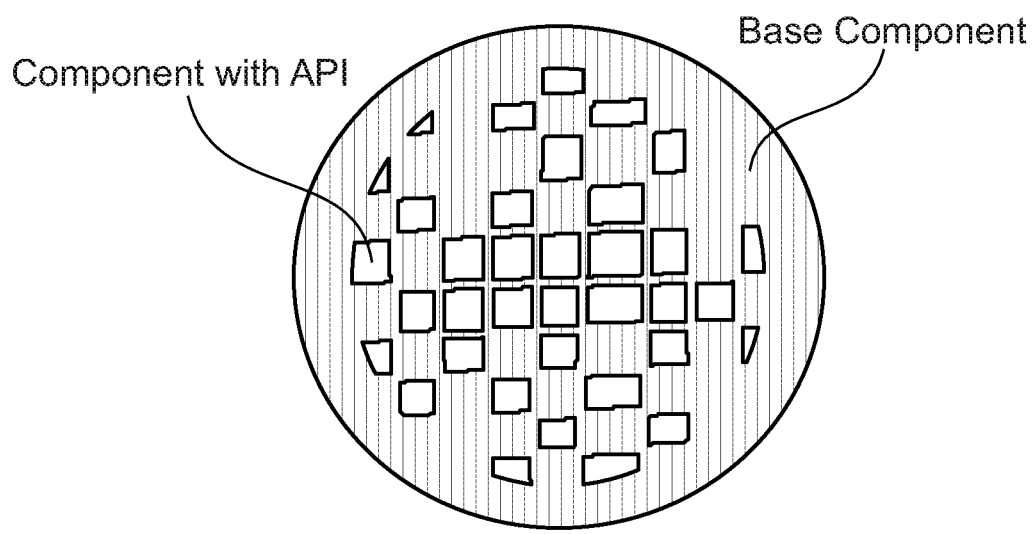
Figure 2:
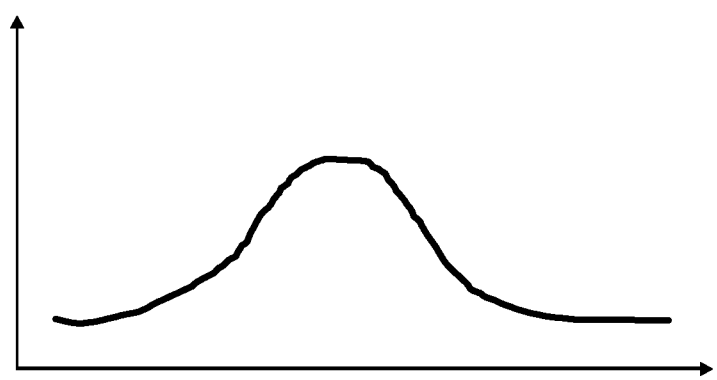
Figure 3:
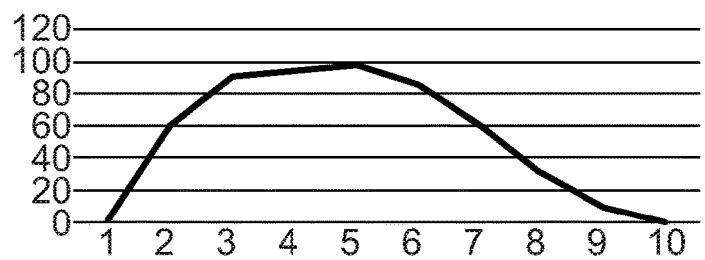
Figure 3:
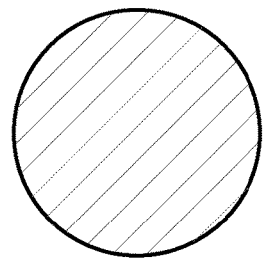
Figure 3:
Figure 3:
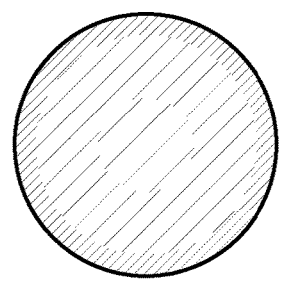
Figure 3:
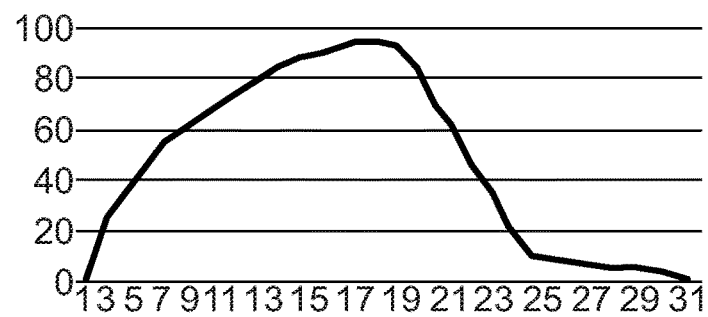
Figure 3:
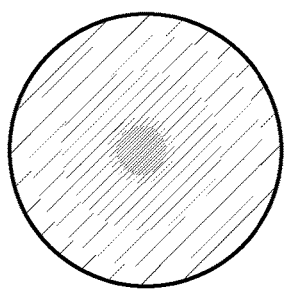
Figure 4:
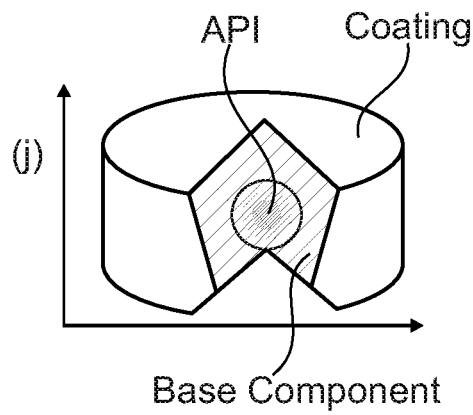
Figure 4:
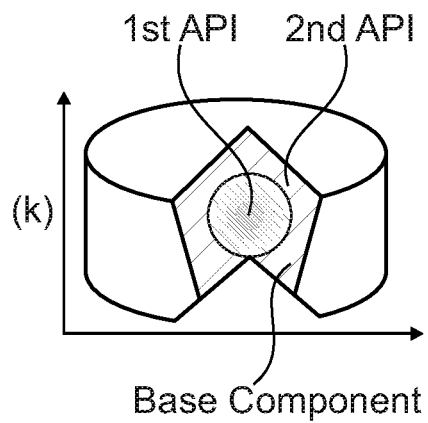
Figure 4:
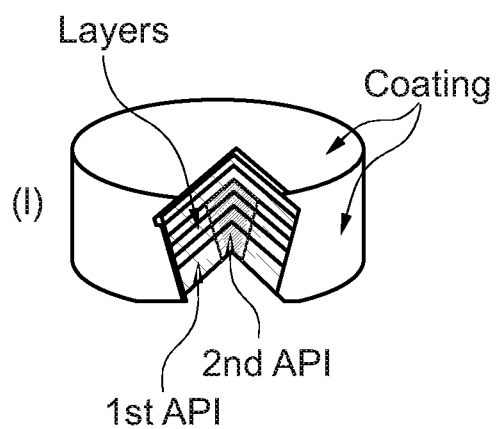
Figure 4:
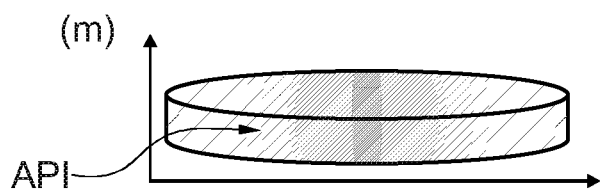
Figure 5:
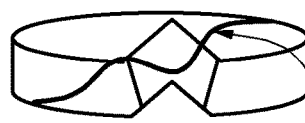
Figure 5:
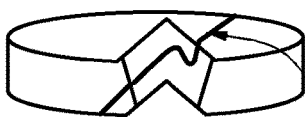
Figure 5:
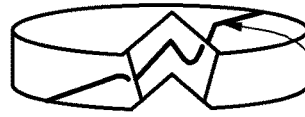
Figure 5:
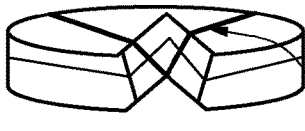
Figure 6:
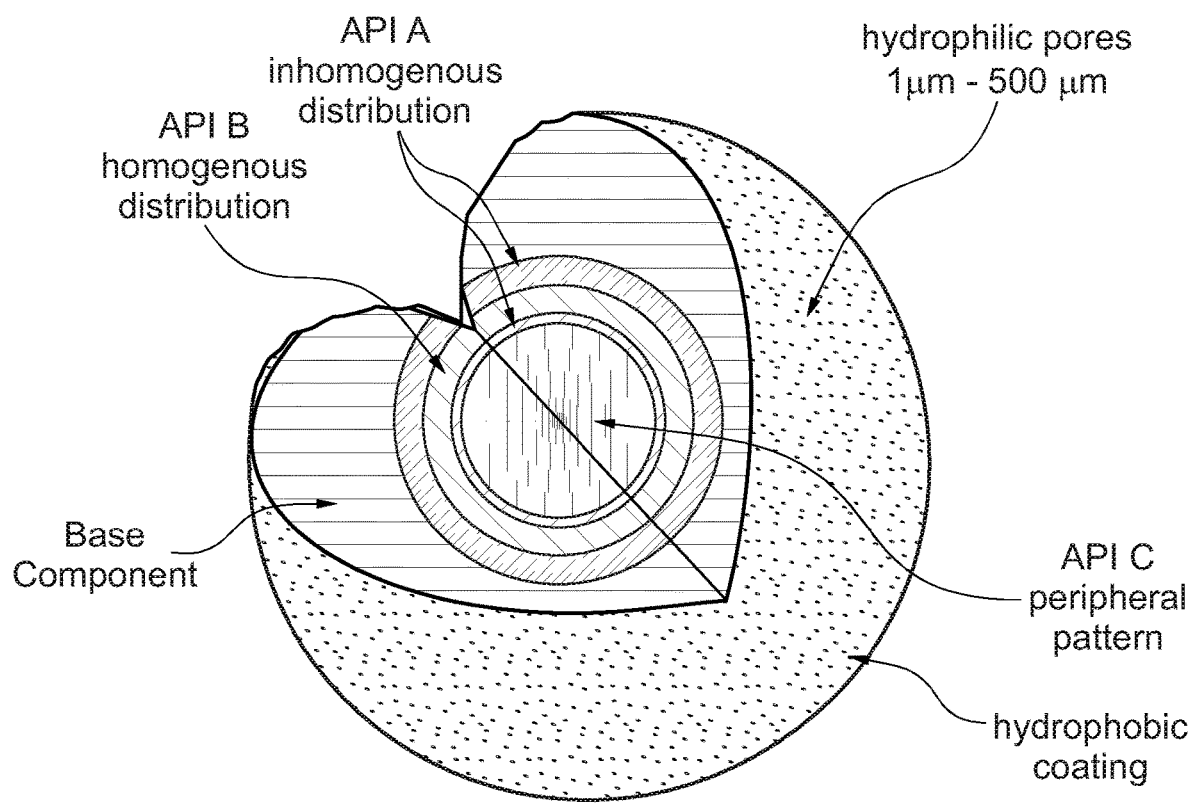
Figure 7:
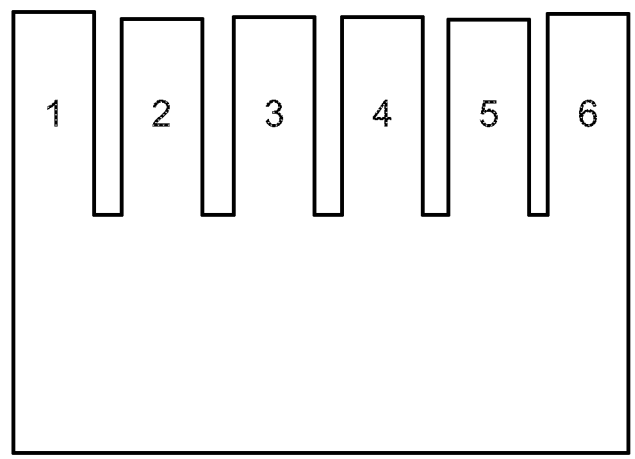

In the following, the present invention will be described with reference to the enclosed figures. It shows:

FIG. 1 several designs of drug delivery systems according to the present invention;

FIG. 2 a further design of a drug delivery system and respective concentration profile according to the present invention;

FIG. 3 several API release profiles of drug delivery systems according to the present invention;

FIG. 4 further designs of drug delivery systems according to the present invention;

FIG. 5 further designs of drug delivery systems according to the present invention;

FIG. 6 a further design of a drug delivery system according to the present invention; and FIG. 7 a structured drug delivery system according to the present invention.

FIG. 1 illustrates nine design options for drug delivery systems according to the present invention. As can be seen, all these designs comprise a base component, which forms the overall body of the respective drug delivery system (DDS) and can be considered as a matrix, within which further components may be arranged. These further components are labeled as component A, component B, component C, and component D, and may each comprise a therapeutically effective amount of a separate active pharmaceutical ingredient (API). Thus, any of the components A-D may be considered as a first component within the context of the present invention. The base component and the components A-D are soluble in body fluids.

The design of DDS (a) in FIG. 1 has a round shape. DDS (a) may be in a form of a tablet, a disc or the like. It has a particular diameter D, which may be, for example, 15 mm. Within the base component of the DDS (a), a first component A comprising a first API, a second component B comprising a second API and a third component C comprising a third API are provided. As can be seen, the respective APIs are not distributed homogeneously through the drug delivery system, but are arranged inhomogeneously within the base component, as the components A, B, C are provided at particular positions within the drug delivery system. The components A, B, C are provided in a polygonal shape, with a hexagonal cross section.

Upon application of DDS (a) and dissolution thereof, the base component dissolves first, as the dissolution may begin at the edge of the system. After a particular period of time, component C and then component B start to dissolve, thereby releasing the respective APIs. Later on, component A eventually starts to dissolve, thereby releasing the respective first API provided therein. Thus, due to the particular arrangement of the components in the drug delivery system, the different APIs are released at different stages at different dosages after application of the drug delivery system. Due to the particular arrangement of the different components within DDS (a), each API is released at a particular time after application of the drug delivery system, with a particular and individual, API-specific release profile.

The design of DDS (b) in FIG. 1 is formed as a tablet, with a height of, for example, 2.5 mm, and a diameter of again 15 mm. Two components B and C comprising each an API are provided within the base component in an inhomogeneous manner according to the present invention. Upon application of the system, particular release profiles of the APIs contained in components B and C are obtained, which may feature smooth transitions between phases of increased release.

The design of DDS (c) in FIG. 1 is similar to that of DDS (a), however comprising, beside the base component, only two components B and C comprising each an API. Upon application of the system, particular release profiles of the APIs contained in components B and C are obtained, which may feature smooth transitions between phases of increased release.

In the design of DDS (d) in FIG. 1, two components with APIs are provided in a tube-like shape. Similarly, the components may also be provided in form of stacked plates.

DDS (e) in FIG. 7 has a design where the components comprising APIs are provided as spots within the base component. Upon application of the system, particular release profiles of the APIs contained in components B and C are obtained, which may feature smooth transitions between phases of increased release.

DDS (f) in FIG. 1 has a design of a particular heights of, for example, 25 mm, wherein only one component comprising an API is arranged inhomogeneously in the base component, in a tube-like manner. Similarly, the component may also be provided in form of plates.

DDS (g) in FIG. 1 is similar to DDS (e), however the components comprising APIs are arranged in a more random manner. Upon application of the system, particular release profiles of the APIs contained in components B and C are obtained, which may feature smooth transitions between phases of increased release.

DDS (h) in FIG. 1 has a design, where the components comprising the APIs are provided or arranged in the form of circles within the base component. Upon application of the drug delivery system, the base component and the first component dissolve in an alternating manner, such that the first API is released intermittently, for example in a rather periodic manner. After the first API is completely released, the second component starts dissolving, thereby releasing the second API. As can be seen, the circles of component A are not concentric, and are not having a uniform thickness. Due to this particularly inhomogeneous arrangement, a particular release profile is obtained, which may feature smooth transitions between phases of increased release.

DDS (i) in FIG. 1 has a design where a component comprising an API is provided in a particular pattern within a matrix of additives, which is arranged in the base component.

The person skilled in the art understands that each of the systems described above with regard to FIG. 1 has particular release characteristics with regard to the API(s) provided therein. Depending on the therapeutic application, the person skilled in the art understands to choose an appropriate design, with an inhomogeneous arrangement of the API in the base component according to the present invention.

FIG. 2 shows a further design of a drug delivery system according to the present invention. Therein, the component comprising the API and the base component are arranged on a grid-like structure, with each "pixel" defined either by the API component or the base component. As can be seen, the two components are arranged such that the density of "API-pixels" is higher at a central part of the drug delivery system. This is also apparent from the API concentration profile, which is also illustrated in FIG. 2. The profile features a peak of high API concentration at the center of the system, and low API concentration at the edges of the system. The transition from the low API concentration at the edges to the high API concentration at the center is smooth, as it does not feature any abrupt steps. With such a drug delivery system, the release profile of the system upon dissolution of the two components is adjusted or configured in a desired manner.

FIG. 3 shows the release profile of a common drug delivery system with a homogeneously distributed API (graph (1) in FIG. 3), as well as two release profiles of drug delivery systems according to the present invention (graphs (2) and (3) in FIG. 3). The design of the respective drug delivery system is shown next to the graphs. The drug delivery systems are provided in a round shape, and may be a tablet dissolving upon oral administration, for example. The respective graphs each show the release of the API of the respective drug delivery system over time.

Regarding graph (1) in FIG. 3, the design of the respective drug delivery system is such that the API is homogeneously distributed throughout the system. This principle of homogeneity, which is the key feature of common prior art drug delivery systems, derives from the corresponding manufacturing processes. Upon dissolution of classical drug delivery systems, the respective API is released. Due to the dissolution characteristics of the homogeneous system and the shape of the system, a particular and fixed release profile is obtained. As can be seen from graph (1) in FIG. 3, the release of the API increases gradually over time, reaches a maximum, and thereafter decreases gradually.

Due to the inhomogeneous arrangement of the API according to the present invention, different release profiles can be obtained. The design associated with graph (2) in FIG. 3 is different from that associated with graph (1) in FIG. 3, as the API is arranged at an edge of the drug delivery system. Hence, the principle of a homogeneous distribution of the API in the system is suspended, as the API is inhomogeneously arranged in the system, being provided here with a high concentration at the edge of the system. The concentration of the API smoothly decreases towards the center of the system. Upon application of the drug delivery system associated with graph (2) of FIG. 3, the release of the API is rather high in the beginning and then decreases gradually. Such a high initial API release may be beneficial for particular applications, as will be appreciated by the person skilled in the art.

In the design associated with graph (3) in FIG. 3, the API is accumulated at a central part of the drug delivery system. Thus, the concentration of the API is highest at the center of the system, and the gradient of the concentration points from the edge of the system to its center. As can be seen from the respective graph (3) in FIG. 3, the release increases approximately gradually over a prolonged period of time, and the maximum release rate is delayed in time as compared to the common design. In comparison to the common design, the release of the API can be considered to be more constant, for an extended period of time. Such a release profile may be beneficial for particular applications, as will be appreciated by the person skilled in the art.

FIG. 4 shows further design options for a drug delivery system according to the present invention. The overall shape of the systems is that of a round disk with a diameter of 5-25 mm, preferably 20 mm or 15 mm, and a thickness of 0.5-15 mm, preferably 2 mm or 6 mm. A cut into the tablets is provided to allow for a view on the arrangement of the components in the tablets.

The design of DDS (j) in FIG. 4 has a first component comprising a first API provided at the central part of the tablet, being surrounded by a base component, while the entire tablet is coated with a coating. The coating may be a hydrophilic coating, or may provide entericcoated properties, for example. The concentration of the API within the tablet is highest at the center of the tablet. The concentration profile of the API is such that it comprises a smooth transition from the edge of the tablet towards the center of the tablet.

The design of DDS (k) in FIG. 4 has a first component comprising a first API and a second component comprising a second API being provided within a base component. Again, also a coating is provided. The second component is arranged in the form or a sphere, and the concentration of the second API is highest on the surface of the sphere, decreasing smoothly towards the center of the sphere. Within the sphere formed of the second component, the first component is provided. Thus, upon application of the tablet and dissolution of the components, the second API is released prior to the first API, and during a transition period, both APIs are released.

The design of DDS (l) in FIG. 4 has two different APIs, with the second API being provided at a central part of the tablet, and the first API is provided around the second API. At an interface region between both APIs, there is an overlap of the APIs, such that in this interface region, both APIs are arranged. Thereby, a smooth crossover is achieved. Furthermore, layers are provided, extending through the system, which may be hydrophobic layers.

The design of DDS (m) in FIG. 4 does not have a coating. An API is inhomogeneously arranged in the tablet, such that areas or regions with different concentrations of the API are formed.

FIG. 5 shows further design options for a drug delivery system according to the present invention. The overall shape of the systems is that of a round disk with a particular thickness. As can readily be recognized, the systems comprise one or more markings being arranged at least partially on the surface of the tablets. The markings form a visible two-dimensional pattern on the surface of the tablets. As shown in FIG. 5, the pattern of the marking may be a discontinuous pattern. The pattern may comprise smooth curves, or sharp edges. Accordingly, the pattern may be arranged in an inhomogeneous manner. The markings may be formed by a particular marking component, or a component comprising an API. By providing drug delivery systems with such elaborate markings, particular security features are created which allows for a user to authenticate the origin of the drug delivery system.

FIG. 6 illustrates a further design option for a drug delivery system according to the present invention. The system is provided in a spherical shape, and has a hydrophobic coating. The coating comprises hydrophilic pores with sizes in the range of 1 μm to 500 μm. Inside the drug delivery system, there is provided a base component and three different active pharmaceutical ingredients, API A, API B, and API C. The API C is provided at a central part of the system with a peripheral pattern. The other two APIs A and B surround API C. Thereby, API B is provided as a hollow sphere, with a homogeneous distribution of the API. Furthermore, API A is inhomogeneously distributed, surrounding the API C. Thereby, the concentration of API A diminishes towards an edge of the illustrated drug delivery system.

FIG. 7 illustrates a cross-section of a drug delivery system according to the present invention. As can be depicted, the surface of the drug delivery system is structured, as six protrusions and respective recesses in between are formed on one side thereof. By increasing the surface in this manner, the dissolution of the drug delivery system and thus the release of the API can be enhanced. The person skilled in the art understands that the entire surface of the drug delivery system, or only one or several parts thereof may be structured.

Therefore, the person skilled in the art understands that with the drug delivery system according to the present invention, a particular inhomogeneous distribution of one or more APIs within the system can be arranged in order to provide a desired release of the API(s). The person skilled in the art understands that a prompt release or a delayed release of an API can be obtained. Furthermore, it is possible to release a particular single API at different dosages over a prolonged period of time, for example intermittently, thereby obtaining a release of the API(s) in phases.

Furthermore, it is possible to obtain a release of different APIs in distinct phases with a single, novel drug delivery system. For example, it is possible to design the system such that a first API is released before a second API is released. Examples for such systems integrating two or potentially more APIs include gastroprotective agents such as proton pump inhibitors or antihistamines and non-steroidal anti-inflammatory substances such as ibuprofen or diclofenac. Another example would be the combination of antiemetics (e.g. ondansetron, domperidon) and analgesics, especially those acting on structures of the central nervous system (e.g., tramadolhydrochloride). Another example would be the combination of Carbidopa and Levodopa, thus an agent that prevents the degradation of the pharmaceutically active ingredient. The person skilled in the art understands that the release of these two APIs may provide particular synergetic effects. Furthermore, controlled release could mean mimicry of physiology, e.g. a Cortisone therapy whereas the drug delivery system is administered at 10:00 μm, preferably releasing the steroid 6 hours later. As the steroid is desirably administered at 4:00 am, it is possible to administer the steroid with the drug delivery system according to the present invention, which can be designed such that it is ingested in the previous evening, but the respective API is released at the desired time during the night. Similarly, with the drug delivery system according to the present invention, it is possible to ensure a proper administration of antibiotics in phases, for example, over a prolonged period of time (e.g. over days). Thus, the negative effects of patients disregarding the prescribed administration routine can be reduced.

The design options resulting from the concept of an inhomogeneous arrangement of one or more APIs in a drug delivery system are numerous. The person skilled in the art understands that the above examples can be combined to obtain further elaborate designs with release profiles optimized to the particular application or therapy.

The invention claimed is:

1. A drug delivery system for a controlled administration of an active pharmaceutical ingredient, API, to a body, the system comprising:

a base component soluble in body fluids, a separate first component soluble in body fluids, and
a separate second component soluble in body fluids,
wherein the first component comprises a therapeutically effective amount of a first API,
wherein the second component comprises a therapeutically effective amount of a second API,
wherein the first component and the second component are inhomogeneously arranged in the base component,
wherein the first component or a separate marking component is optically different from the base component and arranged such that it forms a two-dimensional pattern on the surface of the system.

2. The system of claim 1, wherein the base component is provided as a three-dimensional body, and wherein the separate first component is inhomogeneously arranged throughout the base component.

3. The system of claim 1, wherein the concentration of the first API varies throughout the system.

4. The system of claim 1, wherein the concentration of the first API is highest at a center of the system.

5. The system of claim 1, wherein a gradient of the concentration of the first API increases towards a center of the drug delivery system.

6. The system of claim 1, wherein a concentration profile of the first API throughout the system comprises a smooth transition to an area of increased concentration.

7. The system of claim 1, wherein a concentration profile of the first API throughout the system comprises more than one area of increased concentration.

8. The system of claim 1, wherein the variation of the concentration of the first API throughout the system is at least 5%.

9. The system of claim 1, wherein the variation of the concentration of the first API throughout the system is at most approximately 100%.

10. The system of claim 1, wherein the concentration profile of the first API is such that upon application of the system, the first API is released from the system at a predetermined release profile.

11. The system of claim 1, wherein the concentration profile of the first API is such that upon application of the system, the first API is released at two or more dosages, wherein release of the first API at one of the dosages starts 1 second to 10 days before release of the first API at another one of the dosages.

12. The system of claim 1, wherein the base component envelops the system and the first component is not arranged at an outer face of the system.

13. The system of claim 1, wherein a concentration profile of the first API throughout the system is different than a concentration profile of the second API throughout the system.

14. The system of claim 1, wherein the first component and the second component are arranged in the system such that upon application of the system, release of the first API starts before release of the second API, wherein the release of the first API starts 1 second to 10 days before release of the second API.

15. The system of claim 1, wherein the first component and the second component are arranged in the system such that upon application of the system, a release profile of the first API differs from a release profile of the second API.

16. The system of claim 1, wherein the two-dimensional pattern is visible from the outside.

17. The system of claim 1, wherein the two-dimensional pattern allows for authentication of the origin of the drug delivery system.

18. The system of claim 1, wherein the two-dimensional pattern is a discontinuous pattern.

* * * * *